US006350122B1

(12) United States Patent
Meyer

(10) Patent No.: US 6,350,122 B1
(45) Date of Patent: Feb. 26, 2002

(54) DENTAL MATRIX WITH LATERAL ILLUMINATION PORTS

(75) Inventor: Alvin Meyer, San Mateo, CA (US)

(73) Assignee: Dentsply International Inc.

( * ) Notice: Subject to any disclaimer, the term of this patent is extended or adjusted under 35 U.S.C. 154(b) by 0 days.

(21) Appl. No.: 09/354,019

(22) Filed: Jul. 15, 1999

(51) Int. Cl.$^7$ .............................................. A61C 5/04
(52) U.S. Cl. ............................................................ 433/39
(58) Field of Search .................................. 433/39, 40, 44, 433/43, 36, 37

(56) References Cited

U.S. PATENT DOCUMENTS

| | | | |
|---|---|---|---|
| 1,255,109 A | | 1/1918 | Russ |
| 1,336,746 A | | 4/1920 | Ivory |
| 2,310,448 A | | 2/1943 | Leib ................................ 32/63 |
| 2,567,101 A | * | 9/1951 | Carpenter ...................... 433/39 |
| 2,594,367 A | | 4/1952 | Tofflemire ...................... 32/63 |
| 2,607,117 A | * | 8/1952 | Baughan ........................ 433/39 |
| 2,611,182 A | * | 9/1952 | Tofflemire ..................... 433/39 |
| 2,706,333 A | | 4/1955 | Schultz ........................... 32/36 |
| 3,145,472 A | * | 8/1964 | Tofflemire ..................... 433/39 |
| 3,411,214 A | | 11/1968 | Lazarus ........................... 32/63 |
| 3,421,222 A | * | 1/1969 | Newman ....................... 433/36 |
| 3,482,314 A | * | 12/1969 | Tofflemire ..................... 433/39 |
| 4,004,345 A | | 1/1977 | Ely ................................. 32/36 |
| 4,265,623 A | | 5/1981 | Soelberg et al. ............. 433/139 |
| 4,601,622 A | | 7/1986 | Galler .......................... 433/226 |
| 4,639,221 A | | 1/1987 | Sairenji ........................ 433/139 |
| 4,661,063 A | | 4/1987 | Levy ............................ 433/139 |
| 4,718,852 A | | 1/1988 | Galler .......................... 433/148 |
| 4,787,849 A | | 11/1988 | Jacoby et al. ................ 433/139 |
| 5,199,869 A | | 4/1993 | McGann ........................ 433/21 |
| 5,314,331 A | | 5/1994 | Brosius et al. ................. 433/21 |
| 5,330,353 A | | 7/1994 | Wavrin .......................... 433/39 |
| 5,380,198 A | | 1/1995 | Suhonen ........................ 433/39 |
| 5,425,635 A | * | 6/1995 | Croll ............................. 433/39 |
| 5,503,556 A | | 4/1996 | Leonard et al. ............. 433/139 |
| 5,607,302 A | | 3/1997 | Garrison et al. ............... 433/39 |
| 5,730,592 A | * | 3/1998 | Meyer ........................... 433/39 |
| 5,788,487 A | | 8/1998 | Meyer ........................... 433/39 |
| 5,788,496 A | | 8/1998 | Marlinghaus ................ 433/215 |
| 5,788,499 A | | 8/1998 | Hoffman ...................... 433/226 |
| 5,803,731 A | | 9/1998 | Nordström .................... 433/96 |
| 5,807,101 A | | 9/1998 | Scalzo .......................... 433/39 |
| 5,813,856 A | | 9/1998 | Lee ............................... 433/31 |
| 5,813,857 A | | 9/1998 | Hertz ............................ 433/93 |

FOREIGN PATENT DOCUMENTS

WO    98/43596    10/1998

* cited by examiner

*Primary Examiner*—Todd E. Manahan
(74) *Attorney, Agent, or Firm*—James B. Bieber

(57) ABSTRACT

A dental matrix for containing a light curable composite restorative inserted in a prepared tooth is provided including a contour portion and flange portions for engaging the tooth and composite restoration. A flange portion is provided with a port positionable to allow a curing light beam to reach the restorative to induce hardening of the composite and influence direction of shrinkage incidental to curing of the composite.

11 Claims, 3 Drawing Sheets

DENTAL MATRIX WITH LATERAL ILLUMINATION PORTS

BACKGROUND

1. Field of Invention

This invention provides a means for dentists to shape portions of restorative materials when filling a tooth cavity, specifically, to form anatomically and functionally realistic contours and to influence the direction of contraction when photo-reactive restoratives are cured within a cavity. The means consists of ports and light reflective panels in the flanges of shims to permit lateral illumination. Embodiments include dimples, marks or notches to clearly indicate the edge nearest to the occlusal, biting, surface of the affected tooth.

BACKGROUND

2. Description of Prior Art

In the course of restoring a tooth damaged by decay a dentist will enucleate the defective tissues and refill the resultant void with prosthetic materials. In their original fluid state the restorative material may flow or sag and thereby fail to restore natural tooth anatomy. Dentists have met that problem by wrapping a thin band, usually steel, around the prepared tooth to temporarily provide a form to contain the restorative in a controlled position until it has solidified. Such bands are referred to as "matrices".

Many restoratives used are photo-reactive polymers known as "composites". Composites may be stimulated to polymerize and become solid by projecting light upon and into the fluid mass. There is a shrinkage of volume to be expected with polymerization. It is desirable that the restorative shrink toward the residual tissues to preclude openings and leakage at the composite-to-tissue interface. The ports disclosed in this invention provide the dentists with new options for directing a light beam and thereby, for influencing the direction of shrinkage.

Teeth tend to be globular in their zones near the occlusal surfaces and conical or cylindrical near their roots, their gingival zone. The disclosed matrices are formed with an impressed dome in its occlusal areas and a cylindrical form in the gingival zone. The occlusal edge of the matrix is identified by a dimple, notch or imprint.

Various forms have been suggested for matrices. As examples, U.S. Pat. No. 1,255,109 to Russ (1918) describes a metal strip having flanges at one end which may be folded over the other end to girdle the circumference of a tooth. It is opaque and precludes any introduction of light in a horizontal plane. Further, its cylindrical conformation tends to be rigid and to resist the dentist's efforts to reshape the form.

U.S. Pat. No. 2,310,448 to Lieb (1943) describes a thermoplastic ribbon to be wrapped around a tooth. It does not provide the malleability needed to allow the dentist to reshape its form.

U.S. Pat. No. 2,594,367 to Tofflemire (1952) shows a girdling ribbon with an aperture on its lateral aspect designed to permit an injection of restorative into a cheek-side cavity. It does not offer the form or adaptability needed to recreate natural contours on the abutment surfaces nor does it permit horizontal light transmission.

U.S. Pat. No. 3,411,214 to Lazarus (1968) consists of a flattened metal loop encircling the tooth. It does not provide for lateral applications of light nor does it provide the malleability required.

U.S. Pat. No. 5,330,353 to Wavrin (1994) discloses an assembly of a plastic central portion with two metal flanges affixed laterally. It is retained around the tooth by a metal vise which interferes with horizontal light projections. It does not provide natural contours nor does it offer malleability to permit modeling in situ.

U.S. Pat. No. 5,380,198 to Suhonen (1995) describes a matrix having a metal veneer over a plastic base. It does not provide natural contours, requires a vise which limits the horizontal application of light and fails to provide for remodeling.

U.S. Pat. No. 5,788,487 to Meyer (1998) discloses a segmental matrix which does not impose upon untreated approximating surfaces and provides an impressed dome for natural contours but its opaque flanges do not permit a horizontal application of light.

OBJECTS AND ADVANTAGES

Accordingly, several objects and advantages of my invention are:

1. to provide a means and form which will enable an effective reproduction of tooth contours which are natural and functional;
2. to provide a matrix which permits applications of light to the tooth and restorative in horizontal planes;
3. to provide a segmental matrix which is sufficiently malleable to permit secondary adjustments of the shape of the cavity; and;
4. to provide a segmental matrix with a marked and clearly identifiable occlusal edge. Still further objects and advantages will become apparent from a consideration of the ensuing description and drawings.

REFERENCE NUMERALS

| Numeral | Part name |
| --- | --- |
| 12 | Body of a matrix shim |
| 14A, 14B | Perforated flange of shim 12 |
| 16 | Domed central portion of shim 12 |
| 18 | Occlusal (upper) edge of shim 12 |
| 20 | Lower portion of shim 12 |
| 22 | Center, contact portion, of dome 16 |
| 24 | Cylindrical (gingival) portion of shim 12 |

| Numeral | Part name |
|---|---|
| 25 | Gingival wedge (not part of the embodiment) |
| 26A, 26B | Incisions to define outfolding port covers 28A, 28B |
| 28A, 28B | Port covers with reflective undersurfaces 29A, 29B |
| 29A, 29B | Reflective undersurfaces of port covers 28A, 28B |
| 31A, 31B | Ports in flanges 14A, 14B |
| 32 | Dimpled marker at occlusal edge of shim 12 |
| 34 | Notched marker at occlusal edge of shim 12 |
| 36 | Treated tooth, typical |
| 38 | Fold lines of port covers 28A, 28B |
| 40 | Light producing instrument |

SUMMARY

A dental matrix made of shim metal which provides a sectional, kidney-like outline, an upper central domed configuration and a lower central portion which is cylindrical or conical, an impressed marker at its occlusal edge, ports in its lateral flanges, port covers and reflective undersurfaces on said port covers. The term "sectional" indicates that the matrix covers a treated section of a tooth rather than girdle the entire tooth.

PREFERRED EMBODIMENT—DESCRIPTION

Figure 1:
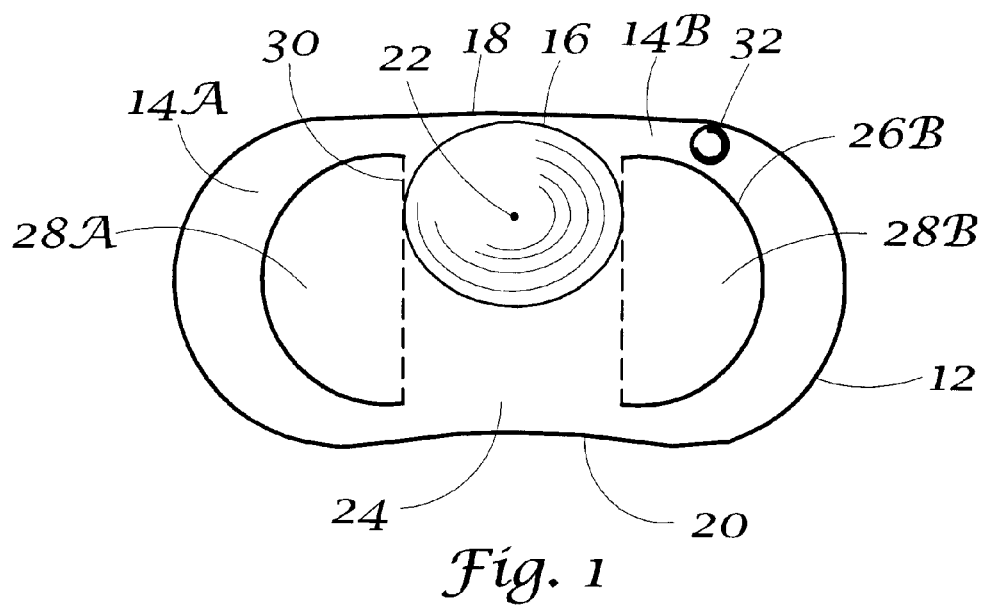
FIG. 1 is a plan view of a segmental matrix with port panels in its lateral flanges in their closed postures and a dimple-marked occlusal edge.

FIG. 1 shows a plan view of symetrical sectional dental matrix 12 die cut and machine shaped of thin and bright shim metal about ⅜ inch tall by about ¾ inch wide by about 0.002 inches thick. Flanges 14A,14B extend laterally from central portion 16 terminating in circular outlines which return toward the midline in a concave arc 20 to show a kidney-shaped outline. Central portion 16 is dome shaped in its upper portion and cylindrical or conical in its lower configuration 24.

Flanges 14A, 14B are incised in a somewhat semicircular outline to define port covers 28A,28B as fold-out port covers and reflectors 29A,29B. Undersurfaces of said port covers 29A, 29B are brightly finished to provide reflective facets. Fold line 38 functions as a hinge to permit an outfolding of port covers 28A,28B.

Flange 14B has a dimple 32, notch 34 or other marker near its convex edge 18 to identify the occlusal edge.

Figure 2:
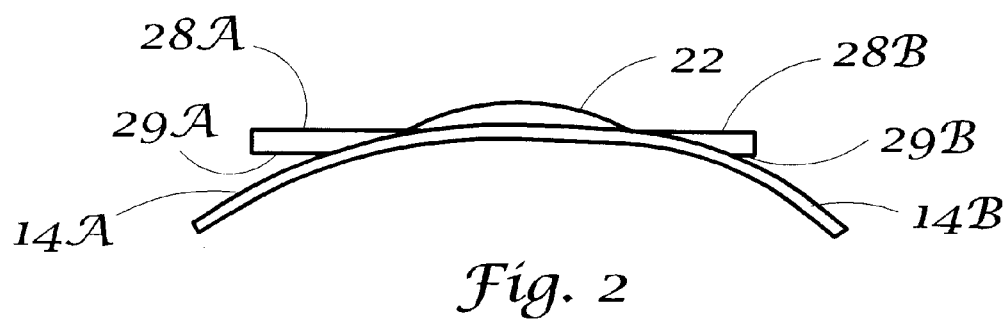
FIG. 2 is an edgewise view of the matrix of FIG. 1.

FIG. 2 is an edgewise view of the embodiment in FIG. 1 with port covers 28A,28B in nearly closed positions.

Figure 3:
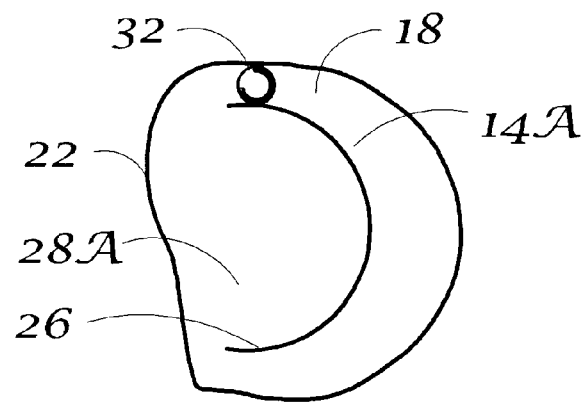
FIG. 3 is a lateral view of the matrix of FIG. 1.

FIG. 3 shows and elevation of matrix 12 of FIG. 1 with port covers 28A,28B nearly closed.

Figure 4:
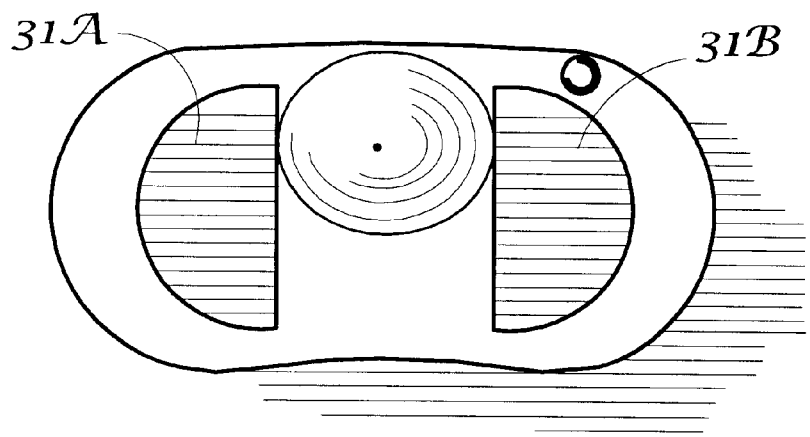
FIG. 4 shows a plan view of a matrix with ports that have no covers.

FIG. 4 is a plan view of an embodiment which has ports 31A,31B without covers, hinges or reflectors.

Figure 5:
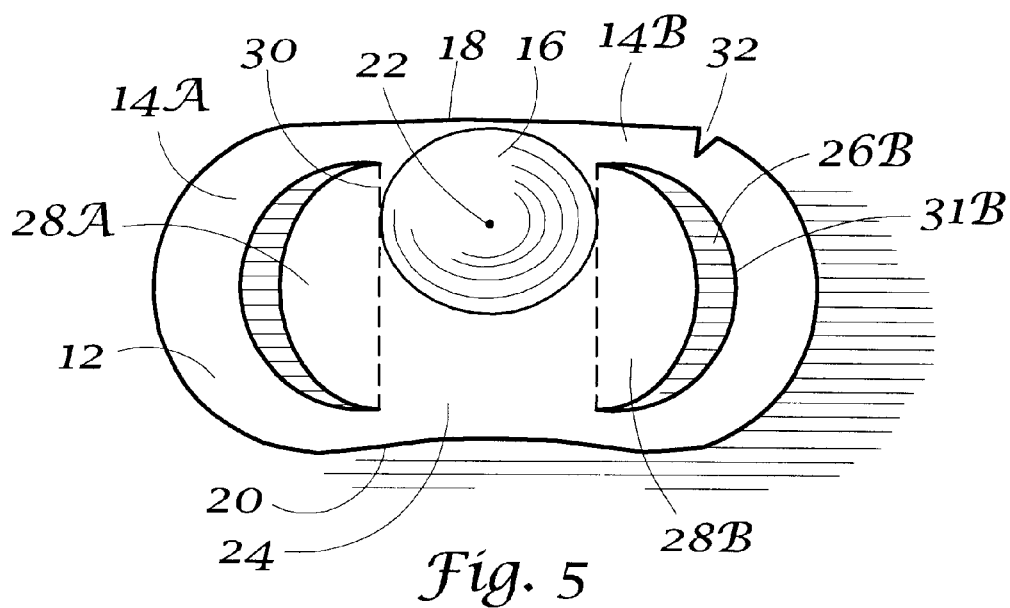
FIG. 5 is a plan view of a matrix with port covers partially open.

FIG. 5 is plan view of an embodiment as in FIG. 1 with port covers 28A, 28B partially folded out along hinge line 38A,38B to expose ports 31A,31B and to position reflective surfaces 29A,29B.

Figure 6:
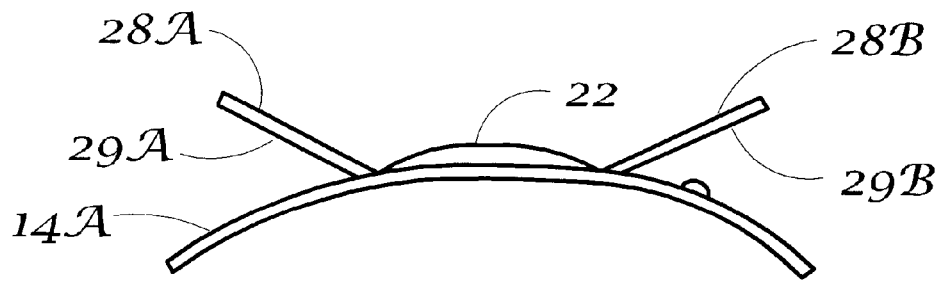
FIG. 6 is an edgewise view of a matrix with port covers partially open.

FIG. 6 is an edgewise view of the embodiment of FIG. 5 with open port covers.

Figure 7:
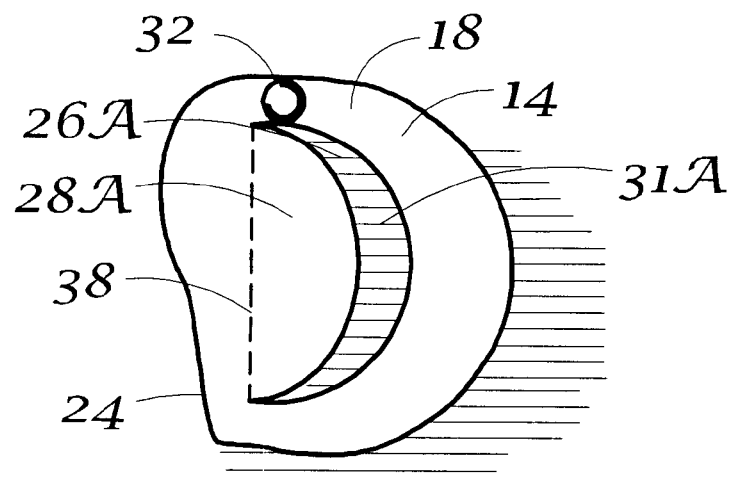
FIG. 7 is a lateral view of a matrix with port covers partially open.

FIG. 7 is a lateral view of the flanges as shown in FIG. 5 with opened port covers.

Figure 8:
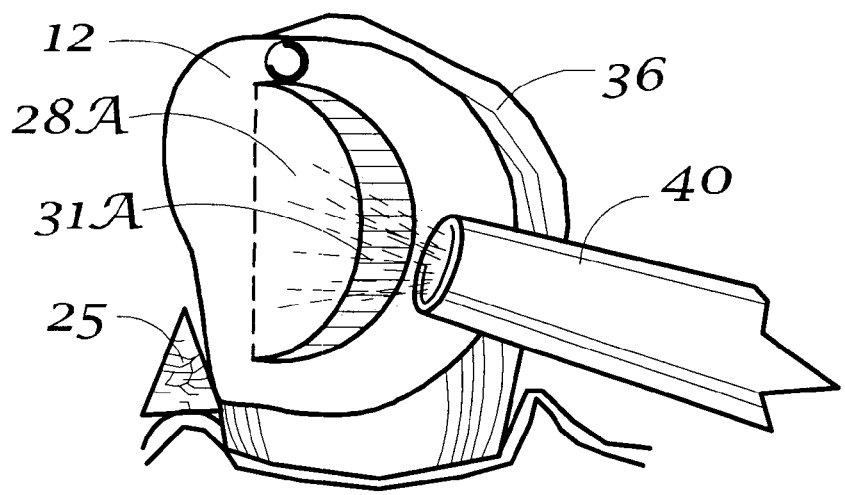
FIG. 8 is a lateral view of a matrix placed around a tooth with a light shining on the port and on the reflective port cover.

FIG. 8 is a lateral view as in FIG. 7 in position on tooth 36 and with a light producer directed toward port 31A and reflector 29A.

PREFERRED EMBODIMENT—APPLICATION

In its preferred embodiment a tooth cavity is cleansed and medicated. Matrix 12 is sterilized and finger rolled to approximate the outer curvature of treated tooth 36. Port covers 28A, 28B will be useful in adapting flanges 28A,28B to tooth 36. Matrix 12 is positioned and inclined to place dome center 22 against the contact point of an abutment tooth. Gingival edge 24 may be forcefully closed by an insertion of a wedge 25 into the interproximal space.

Port covers 28A, 28B are lifted to expose the lateral aspect of tooth 36. A quantity of light reactive composite is placed within the cavity and against the lateral wall of said cavity. Light 40 is projected through port 31A through the tooth residue and into the composite mass to initiate polymerization. Characteristically, the shrinkage of composite, incidental to polymerization, will direct itself toward the light source and thereby produce an intimate adaptation at the interface of composite-to-tooth. The procedure is repeated against the opposite cavity wall to fill most of the cavity. The remaining cavity space is filled with subsequent applications of composite.

Wedge 25 and matrix 12 are withdrawn to permit the polishing of the restoration.

CONCLUSIONS, RAMIFICATIONS AND SCOPE

Accordingly, it can be seen that I have provided a sectional dental matrix with unique ports in its lateral flanges with covers that may be folded out to permit a beam of appropriate light to traverse the residue of a prepared tooth and thereby cause an inserted mass of composite restorative material to harden and contract toward a cavity wall. Port covers will collect and reflect stray light onto the same illuminated tooth residue to support the power of the directed beam.

Although the description above contains many specificities, these should not be construed as limiting the scope of the invention but as merely providing illustrations of some of the presently preferred embodiments of this invention. Various other ramifications are possible within its scope. For examples, the port covers may have alternative shapes and extend beyond the edges of flange margins, port covers may be treated to alter the character of reflected light or the reflective surfaces may be indented in the manner of a fresnel lens to focus the gathered light. Thus, the scope of the invention should be determined by the appended claims and their legal equivalents rather than by the examples given.

I claim:

1. A dental matrix for forming the shape and position of an inserted photo-responsive tooth restorative, comprising:
    a shim having an upper central area formed with a contour characteristic of an occlusal-proximal shape of a tooth,
    said shim having a lower central area shaped to reproduce a shape characteristic of the gingivo-proximal portion of a tooth,
    said shim formed with at least one flange outward of said contour,
    said flange having a least one port positioned such that a light beam may project through said port upon at least a portion of said photo-responsive tooth restoration.

2. A matrix according to claim 1 in which said lower central portion is a portion of a truncated cone.

3. A matrix according to claim 1 in which said lower portion is a portion of a cylinder.

4. A matrix according to claim 1 in which said shim has an occlusal edge and is formed with a marker adjacent said occlusal edge.

5. A matrix according to claim 4 in which said marker is a notch.

6. A matrix according to claim 4 in which said marker is a dimple.

7. A matrix according to claim 1 which further comprises a cover for said port foldable from a first position substantially covering said port to a second position for projection of said light beam through said portion.

8. A matrix according to claim 7 in which said cover has a bright surface to collect and reflect light toward said restorative beneath said shim.

9. A matrix according to claim 8 in which said cover has a bright surface to collect and reflect light toward said restorative beneath said shim.

10. A dental matrix for forming the shape and position of an inserted photo-responsive tooth restorative, comprising:

a shim having an upper central area formed with a dome shaped with a bulbous contour characteristic of an occlusal-proximal shape of a tooth, and at least one flange outward of said dome, said flange being formed with a port positioned so that a light beam may project through said port and upon a tooth and a restorative beneath said shim.

11. A matrix according to claim 10 in which further comprises a cover for said port foldable from a first position substantially covering said port to a second position for projection of said light beam through said portion.

* * * * *